(12) United States Patent
Butler et al.

(10) Patent No.: US 9,192,726 B2
(45) Date of Patent: Nov. 24, 2015

(54) DRUG DELIVERY DEVICE (75) Inventors: Joseph Butler, Warwickshire (GB); David Moore, Leicestershire (GB); Paul Richard Draper, Worcestershire (GB); Stephen Francis Gilmore, Bristol (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 14/130,032

(22) PCT Filed: Jul. 12, 2012

(86) PCT No.: PCT/EP2012/063623
§ 371 (c)(1),
(2), (4) Date: Dec. 30, 2013

(87) PCT Pub. No.: WO2013/010887
PCT Pub. Date: Jan. 24, 2013

(65) Prior Publication Data
US 2014/0142512 A1 May 22, 2014

Related U.S. Application Data (60) Provisional application No. 61/570,307, filed on Dec. 14, 2011.

(30) Foreign Application Priority Data

Jul. 15, 2011 (EP) .................................... 11174122

(51) Int. Cl.
*A61M 3/00* (2006.01)
*A61M 5/315* (2006.01)
(Continued)

(52) U.S. Cl.
CPC ....... *A61M 5/31551* (2013.01); *A61M 5/31525* (2013.01); *A61M 5/31585* (2013.01);
(Continued)

(58) Field of Classification Search
CPC ............. A61M 2005/2488; A61M 2005/3126; A61M 2205/52; A61M 5/31541; A61M 5/31551; A61M 5/31568; A61M 5/31585; A61M 5/31593; G01D 5/2497; G01D 5/25
USPC .......................................................... 604/189
See application file for complete search history.

(56) References Cited

U.S. PATENT DOCUMENTS

2007/0123829 A1 5/2007 Atterbury et al.
2011/0270214 A1* 11/2011 Jorgensen et al. ............ 604/500

FOREIGN PATENT DOCUMENTS

WO 2006/045523 5/2006
WO 2007/116090 10/2007
(Continued)

OTHER PUBLICATIONS

International Search Report for Int. App. No. PCT/EP2012/063623, completed Oct. 31, 2012.

*Primary Examiner* — Kevin C Sirmons
*Assistant Examiner* — Deanna K Hall
(74) *Attorney, Agent, or Firm* — McDonnell Boehnen Hulbert & Berghoff LLP (57) ABSTRACT A drug delivery device is presented comprising of a housing, a plurality of contacts, and a cylindrical member configured to be rotatably supported inside the housing, wherein the outer surface of the cylindrical member is provided with a plurality of tracks together forming an encoder, each track comprising conductive segments and non-conductive segments, and wherein the cylindrical member is supported in the housing such that each track is engaged by a respective one of the plurality of contacts.

14 Claims, 9 Drawing Sheets (51) Int. Cl.
   *G01D 5/249* (2006.01)
   *G01D 5/25* (2006.01)
   *A61M 5/24* (2006.01)
   *A61M 5/31* (2006.01)
(52) U.S. Cl.
   CPC ....... *A61M5/31593* (2013.01); *A61M 5/31595* (2013.01); *G01D 5/2497* (2013.01); *G01D 5/25* (2013.01); *A61M 5/31541* (2013.01); *A61M 2005/2488* (2013.01); *A61M 2005/3125* (2013.01); *A61M 2005/3126* (2013.01); *A61M 2205/52* (2013.01)

(56) References Cited

FOREIGN PATENT DOCUMENTS

| | | |
|---|---|---|
| WO | 2010/052275 | 5/2010 |
| WO | 2010/098927 | 9/2010 |
| WO | 2010/139640 | 12/2010 |

\* cited by examiner

DRUG DELIVERY DEVICE

CROSS REFERENCE TO RELATED APPLICATIONS

The present application is a U.S. National Phase application pursuant to 35 U.S.C. §371 of International Application No. PCT/EP2012/063623 filed Jul. 12, 2013, which claims priority to European Patent Application No. 11174122.9 filed Jul. 15, 2011 and U.S. Provisional App. No. 61/570,307, filed Dec. 14, 2011. The entire disclosure contents of these applications are herewith incorporated by reference into the present application.

TECHNICAL FIELD

The present invention relates to a drug delivery device.

BACKGROUND

Pen type drug delivery devices have application where regular injection by persons without formal medical training occurs. This is increasingly common among patients having diabetes where self-treatment enables such patients to conduct effective management of their diabetes.

For good or perfect glycemic control, the dose of insulin or insulin glargine has to be adjusted for each individual in accordance with a blood glucose level to be achieved. The present invention relates to injectors, for example hand-held injectors, especially pen-type injectors, that is to injectors of the kind that provide for administration by injection of medicinal products from a multidose cartridge. In particular, the present invention relates to such injectors where a user may set the dose.

A user undertaking self-administration of insulin will commonly need to administer between 1 and 80 International Units.

In medication management, compliance i.e. the degree to which a patient follows medical instructions and protocols, is often of extreme importance. In relation to injection of medicaments, one key aspect of determining the compliance is determination of the actual dose of the medication injected. Another key aspect is determination of the set dose. Accordingly, it is desirable to provide medication delivery devices and/or systems with dose quantity identification systems.

Systems known in the art comprise a detector for providing a signal indicative of an amount of an ejected dose of a drug such that the user may keep a log of the injection history. This kind of system provides information about the actual dispensed dose. However, there is no information available to indicate that the ejected dose is equal to the intended dose. A second sensor would be required to implement this feature.

Other systems known in the art comprise a doseable quantity identifier comprising a rotational matrix and a sensor, wherein a controller circuit interprets the sensed data to determine a quantity of medicine to be delivered. The rotational matrix is often implemented to rotate during dose setting and injection. E.g., the matrix is arranged circumferentially on a sleeve providing absolute positional encoding for one revolution/rotation only. To distinguish between dialing a dose and injection, the processor uses input form an additional separate switch. The switch may be mechanically coupled to a dose button, such that pressing the dose button closes the switch, e.g. via slider, or a barrel having a ramped region. However, implementation is rather complex requiring a dose quantity identifier and a switch arrangement. Both features need to be implemented reliable and resistant against malfunction as well as manufacturing tolerances.

SUMMARY

A first aspect of the invention provides a drug delivery device comprising;
  a housing;
  a plurality of contacts; and
  a cylindrical member configured to be rotatably supported inside the housing, wherein the outer surface of the cylindrical member is provided with a plurality of tracks together forming an encoder, each track comprising conductive segments and non-conductive segments, and wherein the cylindrical member is supported in the housing such that each track is engaged by a respective one of the plurality of contacts.

The cylindrical member may be operationally coupled to the dose setting and delivery mechanism, for example by securing the cylindrical member to a dose dial grip and by having a rotatable engagement between the cylindrical member and an inner housing that is connected to a spindle that is driven during dose administration.

The plurality of tracks may be helical tracks and the housing and the cylindrical member may be configured such that the cylindrical member moves in a first axial direction relative to the housing when rotated in a first rotational direction relative to the housing. The outer surface of the cylindrical member may be provided with seven helical tracks.

The conductive and non-conductive segments of the plurality of tracks may be arranged as a Gray code.

The plurality of tracks may be arranged into first and second banks of tracks.

The conductive segments within each of the first and second banks may be electrically connected to all of the conductive segments in the bank.

The device may further comprise a switch configured:
  in a first position, to electrically connect the first and second banks of tracks; and
  in a second position, to electrically isolate the first and second banks of tracks.

The device may further comprise a user actuated plunger configured to cause expulsion of a drug from the drug delivery device, wherein depression of the plunger may cause the switch to switch from the first position to the second position.

Each contacts may be configured to engage a first segment of each respective track when the cylindrical member is in a first rotational position and each first segment may be a conductive segment.

The device may further comprise;
  a display; and
  a processor configured to receive and interpret electrical signals from the contacts and to control the operation of the display.

The processor may be configured to control application of electrical signals to the contacts. The processor may be configured to cause an electrical signal to be applied to a first one of the contacts and simultaneously to monitor signals at the others of the contacts, and subsequently to cause an electrical signal to be applied to a second one of the contacts and simultaneously to monitor electrical signals at the others of the contacts.

The processor may be configured to apply an electrical signal to each of the contacts relating to the first bank in a sequence and to process the resulting electrical signals at the other contacts to determine whether the switch is closed.

The processor may be configured to determine whether the switch is closed or not closed and relate this status information to the operation mode of the device. The processor may be configured to interpret the information received from the switch to determine the operation mode of the device. The processor may be configured to determine whether the device is in dialing mode or in dispense mode.

The processor may be configured to cause an electrical signal to be applied to at least the first one of the contacts and simultaneously to monitor signals at the others of the contacts in order to determine a position of the cylindrical member. The processor may be further configured to determine a selected drug dose by searching a lookup table providing a conversion from a position of the cylindrical member to a selected drug dose. The processor may be further configured to determine a delivered drug dose by subtracting a remaining drug dose from the selected drug dose.

BRIEF DESCRIPTION OF THE FIGURES

Embodiments will now be described, by way of example only, with reference to the accompanying drawings, in which.

DETAILED DESCRIPTION

Figure 1:
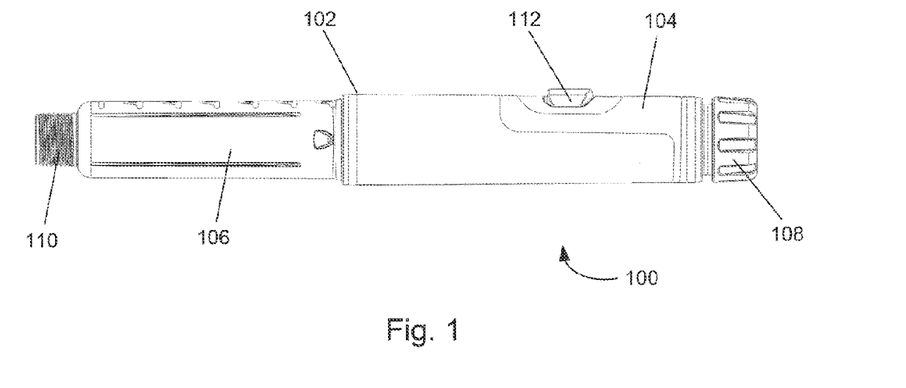
FIG. 1 shows an external view of a drug delivery device suitable for implementing the present invention.

Referring firstly to FIG. 1, an external view of a drug delivery device 100 according to embodiments of the invention is shown. The device 100 shown in FIG. 1 is a pen type injection device, having an elongate cylindrical shape, for setting and delivering a medicament, such as insulin. The device 100 comprises a housing 102 having a first housing part 104 and a second housing part 106. A rotatable dial 108 is located at a first (or proximal) end of the first housing part 104. The rotatable dial 108 has substantially the same outer diameter as the first housing part 104. The second housing part 106 may be detachably connected to the second end of the first housing part 104. The second housing part 106 is configured to have a needle (not shown) or similar drug delivery apparatus attached to it. To achieve this, the second (or distal) end of the second housing part 106 may have a threaded portion 110. The threaded portion 110 may have a smaller diameter than the remainder of the second housing part 106.

A display mount 112 is located on the first housing part 104. A display may be supported on the display mount 112. The display may be an LCD display, a segmented display or any other suitable type of display. The display mount 112 may cover a recess (not shown) in the first housing portion 104. A number of electronic components, described in greater detail with reference to FIG. 2, may be disposed underneath the display mount 112.

The first housing part 104 contains a drug dose setting and delivery mechanism. The second housing part 106 contains a drug cartridge (not shown). The drug contained in the drug cartridge may be a medicament of any kind and may preferably be in a liquid form. The drug delivery mechanism of the first housing part 104 may be configured to engage with the drug cartridge of the second housing part 106 to facilitate expulsion of the drug. The second housing part 106 may be detached from the first housing part 104 in order to insert a drug cartridge or to remove a used cartridge. The first and second housing parts 104, 106 may be connected together in any suitable way, for example with a screw or bayonet type connection. The first and second housing parts 104, 106 may be non-reversibly connected together in such a way as the drug cartridge is permanently contained with the drug delivery device 100. Further the first and second housing parts 104, 106 may form part of a single housing part.

The rotatable dial 108 is configured to be rotated by hand by a user of the drug delivery device 100 in order to set a drug dose to be delivered. The dial 108 may be connected to an internal threading system which causes the dial 108 to be displaced axially from the housing 102 as it is rotated in a first direction. The dial 108 may be rotatable in both directions or only in a first direction. The device 100 is configured, once a drug dose has been set by rotation of the rotatable dial 108, to deliver the set drug dose when a user exerts an axial force at the proximal end of the device. The rotatable dial 108 may support a button (not shown) which must be depressed in order to deliver the set drug dose. The display 112 may be configured to display information on the drug dose which has been set and/or delivered. The display 112 may further show additional information, such as the actual time, the time of the last usage/injection, a remaining battery capacity, one or more warning signs, and/or the like.

Figure 2:
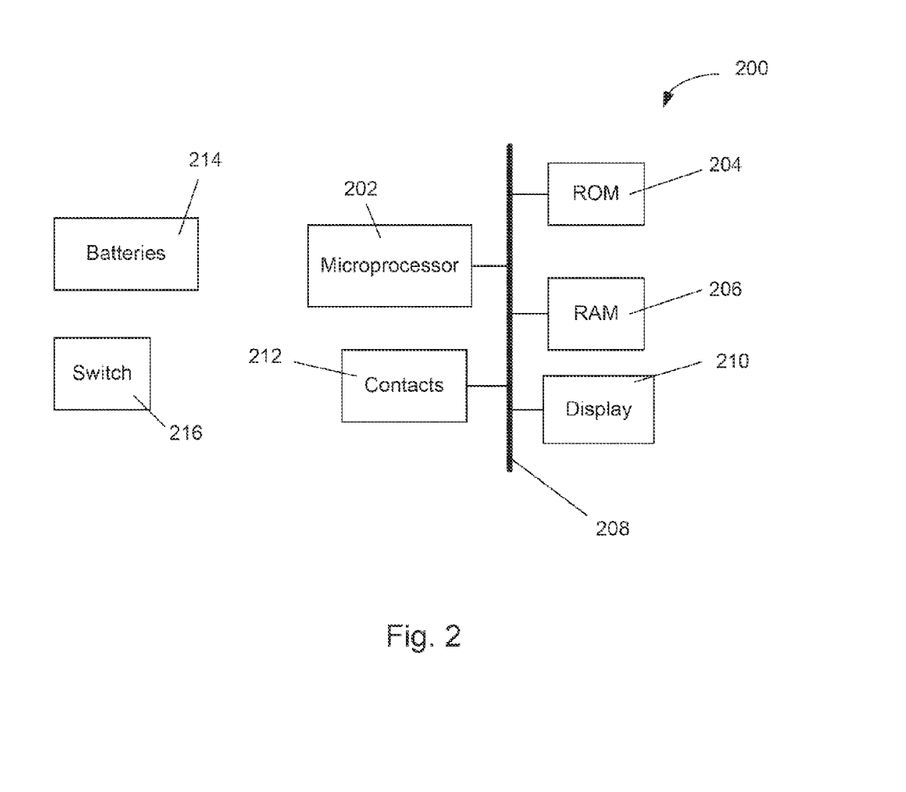
FIG. 2 shows a schematic diagram of some of the electronic components present in the drug delivery device of FIG. 1.

Referring now to FIG. 2, a schematic diagram of electrical circuitry 200 forming part of the drug delivery device 100 is shown. The circuitry 200 comprises a microprocessor 202, a non-volatile memory such as a ROM 204, a volatile memory such as a RAM 206, a display 210, contacts 212 and a bus 208 connecting each of these components. The circuitry 200 also comprises batteries 214 or some other suitable source of power for providing power to each of the components and a switch 216, described in greater detail below.

The circuitry 200 may be integral with the device 100. Alternatively, the circuitry 200 may be contained within an electronic module that can be attached to the device 100. In addition, the circuitry 200 may comprise additional sensors, such as optical or acoustical sensors.

The ROM 204 may be configured to store software and/or firmware. This software/firmware may control operations of the microprocessor 202. The microprocessor 202 utilises RAM 206 to execute the software/firmware stored in the ROM to control operation of the display 210. As such the microprocessor 202 may also comprise a display driver.

The batteries 214 may provide power for each of the components including the contacts 212. The supply of electricity to the contacts 212 may be controlled by the microprocessor 202. The microprocessor 202 may receive signals from the contacts 212 and so could determine when the contacts are energised, and is configured to interpret these signals. Information may be provided on the display 210 at suitable times by operation of the software/firmware and the microprocessor 202. This information may include measurements determined from the signals received by the microprocessor 202 from the contacts 212.

A number of contacts 212 may be present in the device 100. In a preferred embodiment, seven contacts 212 are present and may be addressed individually by the microprocessor. These seven contacts 212 may be arranged into two groups of contacts. In some embodiments, three contacts 212 comprise a first group of contacts and four contacts 212 comprise a second group of contacts. The contacts 212 may be mounted on an inner surface of the housing 102.

Figure 3:
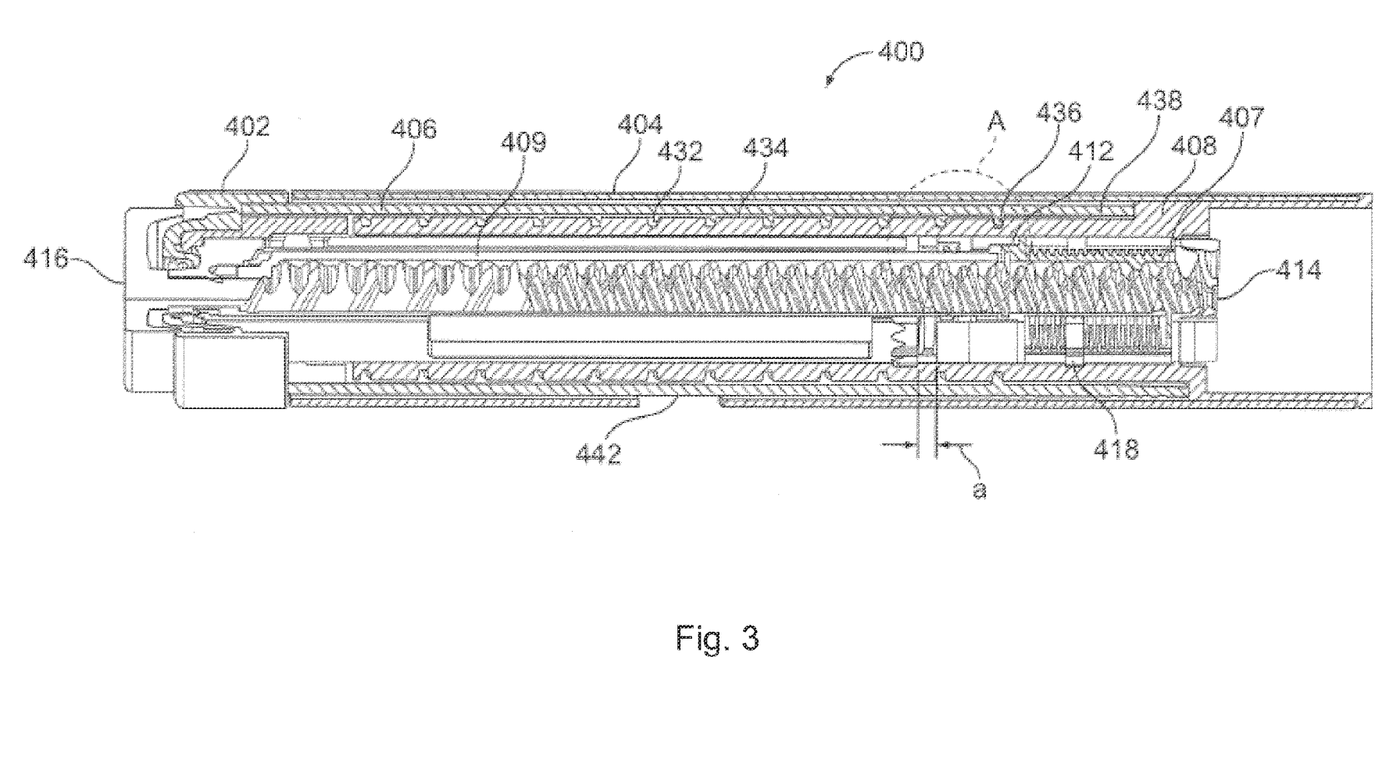
FIG. 3 shows a dose setting mechanism of a drug delivery device suitable for use with the invention.
Figure 4:
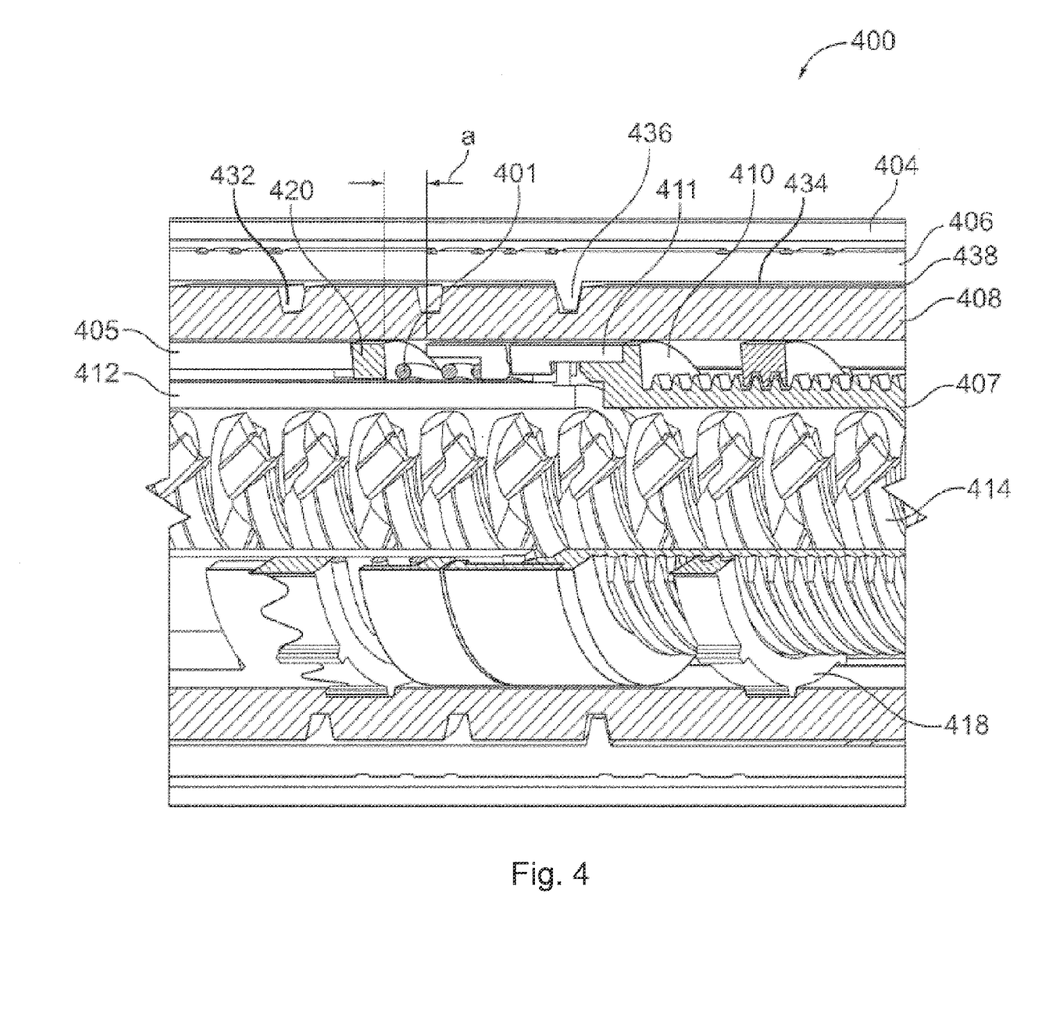
FIG. 4 shows detail of the dose setting mechanism of FIG. 3.
Figure 5:
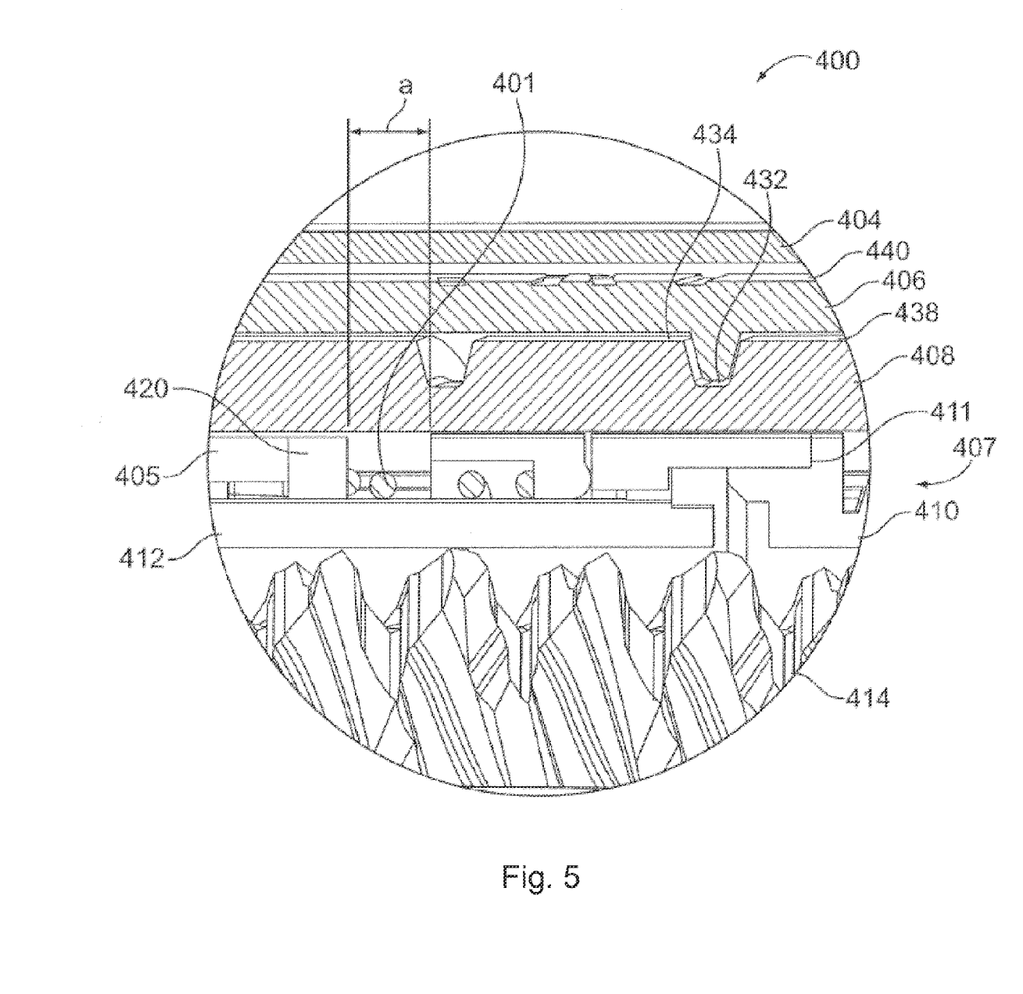
FIG. 5 shows a close up of the region marked 'A' in FIG. 3.

A fuller explanation of the operation of the dose setting and delivery mechanism supported within the second housing part 106 will now be given with reference to FIGS. 3 to 6. FIG. 3 is a cross-sectional view of a dose setting mechanism 400 of a drug delivery device. FIG. 4 is a detailed view of a portion of the dose setting mechanism 400. FIG. 5 illustrates a close up view of the region marked 'A' in FIG. 3.

The dose setting mechanism 400 comprises an outer housing 404, an inner housing 408 and an encoded member 406. These components are preferably hollow cylinders arranged concentrically. The encoded member 406 is disposed between the outer and inner housings 404, 408. The inner housing 408 comprises a groove 432 provided along an external surface 434 of the inner housing 408. A groove guide 436 provided on an inner surface 438 of the encoded member 406 is rotatably engaged with this groove 432. The encoded member 406 has information encoded on its outer surface 440 as will be described in more detail below with reference to FIGS. 7 to 10. The encoded member 406 is of cylindrical shape.

A dose dial grip 402 is located at a proximal end of the outer housing 404. The dose dial grip 402 is disposed about an outer surface of a proximal end of the encoded member 406. An outer diameter of the dose dial grip 402 preferably corresponds to the outer diameter of the outer housing 404. The dose dial grip 402 is secured to the encoded member 406 to prevent relative movement between these two components. The dose dial grip 402 is represented in the external view of FIG. 1 by the rotatable dial 108. The dose dial grip 402 supports a dose button 416 which has a sprung bias in a proximal direction and is configured to be depressed into the dose dial grip 402 by a user of the device 100.

A spindle 414 is disposed centrally within the mechanism 400. The spindle 414 is provisioned with at least one helical groove. In the embodiment depicted, the spindle 414 has two opposite handed overlapping groove forms that preferably extend over at least a majority of a length of the spindle. Each groove form is effectively continuous over a number of turns. In one preferred arrangement, each groove of the spindle engages either a non-continuous helical groove form on a body portion or on a driver. Preferably, either or both a non-continuous thread form on a body and a driver consists of less than one complete turn of thread. A first thread of the spindle 414 is configured to connect with a portion of the inner housing 408.

The dose setting mechanism 400 also comprises a spring 401, a clutch 405 and a driver 409 having a first driver portion 407 and a second driver portion 412. These driver portions 407, 412 extend about the spindle 414. Both the first and the second driver portions 407, 412 are generally cylindrical. The clutch 405 is disposed about the driver 409. In one arrangement, the first driver portion 407 comprises a first component part 410 and a second component part 411. Alternatively, the first driver portion 407 is an integral component part.

With the dose setting mechanism 400, as a user dials a dose with the dose dial grip 402, the metal spring 401 is selected to be strong enough to maintain engagement of both clutched couplings: the clutched coupling between the clutch 405 and the encoded member 406 and clutched coupling between the first driver portion 407 and second driver portion 412. The encoded member 406 is coupled to the dose dial grip 402 such that when a user rotates the dose dial grip 402, the encoded member 406 also rotates. As the encoded member 406 is rotated in a first rotational direction, it moves axially in a proximal direction due to its threaded connection to the inner housing 408.

When the drug delivery device is being dispensed, the user applies an axial load to the dose button 416 located at the proximal end of the mechanism 400. The dose button 416 is axially coupled to the clutch 405 and this prevents relative axial movement. Therefore, the clutch 405 moves axially towards the cartridge end or the distal end of the dose setting mechanism 400. This movement disengages the clutch 405 from the encoded member 406, allowing for relative rotation while closing up the Gap 'a'. The clutch 405 is prevented from rotating relative to a clicker 420 and hence relative to the inner housing 408. However, in this scenario, the coupling between the first driver portion 407 and the second driver portion 412 is also prevented from becoming disengaged. Therefore, any axial load on the spindle 414 only disengages the first and second driver portions 407, 412 when the dose button 416 is not axially loaded. This therefore does not happen during dispense.

A dose limiter 418 (visible in FIG. 4) is provided on first driver portion 407 and in the illustrated arrangement comprises a nut. The dose limiter 418 has an internal helical groove matching the helical groove of the first driver portion 407. In one preferred arrangement, the outer surface of the dose limiter 418 and an internal surface of the inner housing 408 are keyed together by way of splines. This prevents relative rotation between the dose limiter 418 and the housing 408 while allowing relative longitudinal movement between these two components.

Figure 6:
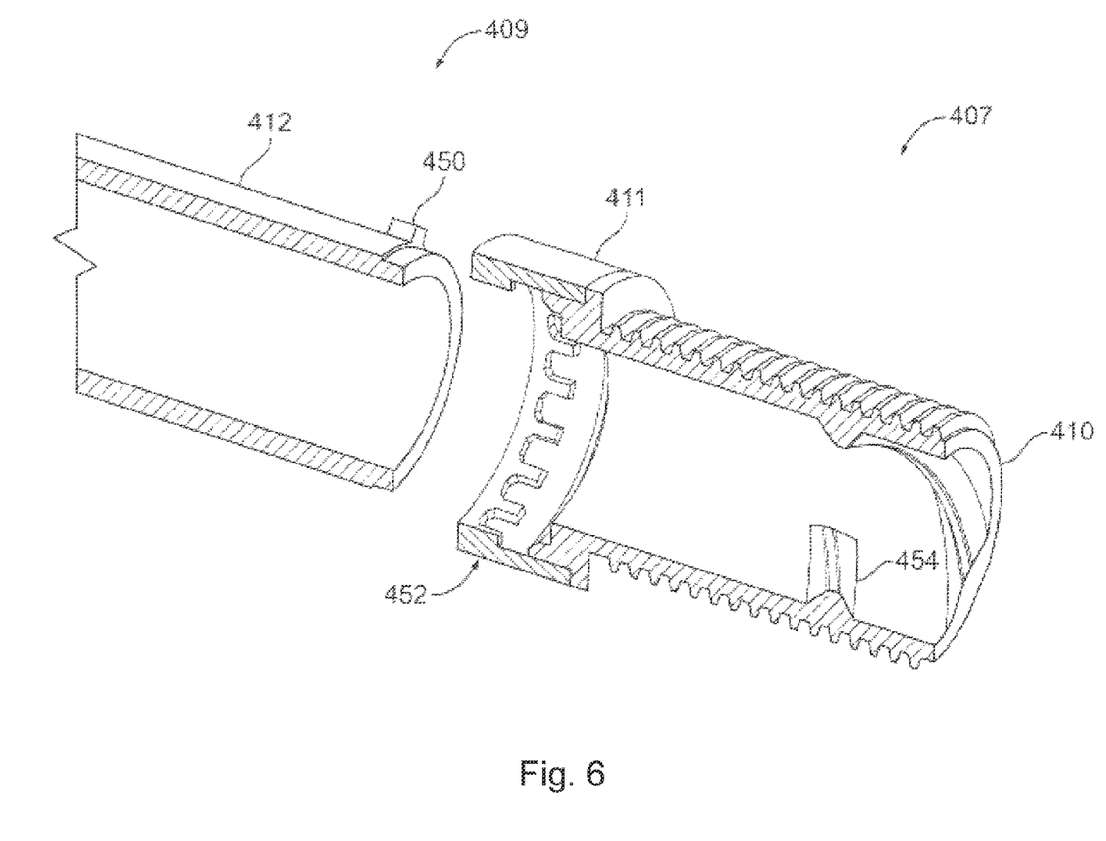
FIG. 6 is an exploded view showing details of a driver forming part of the dose setting mechanism of FIGS. 3 to 5.
Figure 10:
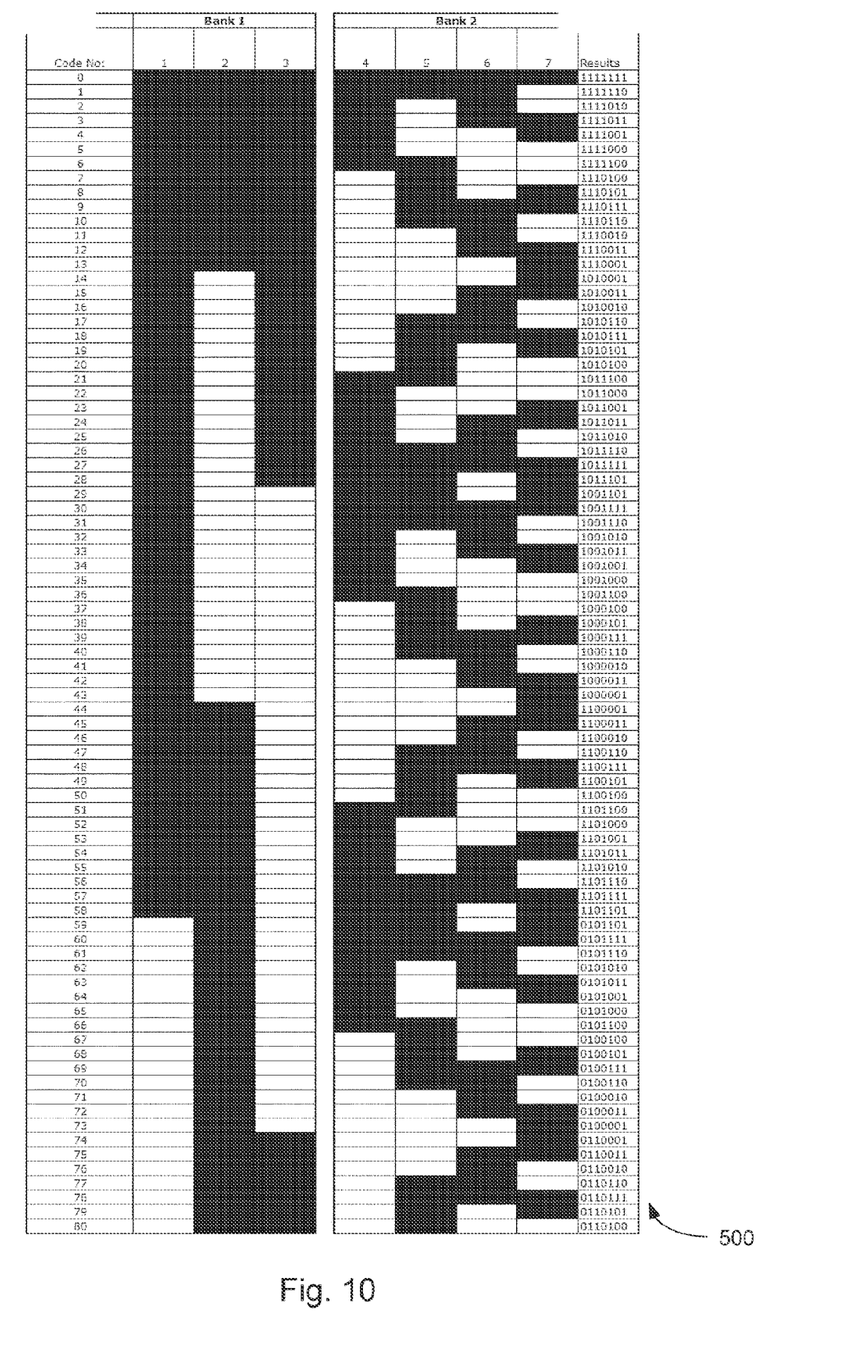
FIG. 10 is a table illustrating a Gray code suitable for use in the invention.

FIG. 6 shows in detail a first arrangement of the first driver portion 407 and the second driver portion 412 illustrated in FIGS. 3 to 5. As illustrated in FIG. 10, the second driver portion 412 is generally tubular in shape and comprises at least one drive dog 450 located at a distal end of the second driver portion 412. The first driver portion 407 also has a generally tubular shape and comprises a plurality of recesses 452 sized to engage with the drive dog 450 on the second driver portion 412. The construction of the drive dog and recesses allow disengagement with the drive dog 450 when the first and second driver portions are axially pushed together. This construction also creates a rotational coupling when these components are sprung apart.

In some embodiments, the first driver portion 407 comprises a first portion (first component part) 410 that is permanently clipped to a second portion (second component part) 411. In this arrangement, the second component part 411 comprises the plurality of recesses 452 and the first component part 410 includes the outer groove for the dose limiter 418 nut as well as an internal groove 454. This internal groove 454 is used to connect to the spindle 414 and drives the spindle 414 during dose administration. In the illustrated embodiment, the internal groove 454 comprises a part helical groove rather than a complete helical groove. One advantage of this arrangement is that it is generally easier to manufacture.

One advantage of this dose setting mechanism 400 utilizing the inner housing 408 is that the inner housing 408 can be made from an engineering plastic that minimizes friction relative to the encoded member 406 groove guide 436 and the groove 432. For example, one such an engineering plastic could comprise Acetal. However, those skilled in the art will recognize that other comparable engineering plastics having a low coefficient of friction could also be used. Using such an engineering plastic enables the material for the outer housing 404 to be chosen for aesthetic or tactile reasons with no friction related requirements since the outer housing 404 does not engage any moving components during normal operation.

The effective driving diameter (represented by 'D') of the grooved interface between the encoded member 406 and the inner housing 408 is reduced compared to certain known drug delivery devices for the same outer body diameter. This improves efficiency and enables the drug delivery device to function with a lower pitch (represented by 'P') for this groove and groove guide connection. In other words, as the helix angle of the thread determines whether when pushed axially, the encoded member will rotate or lock to the inner body wherein this helix angle is proportional to the ratio of P/D.

A recess 442 in the outer housing 404 of the drug delivery device 100 can be seen in FIG. 3. This recess 442 may be configured to receive an insert or electronic module (not shown), comprising the Microprocessor 202, ROM 204, RAM 206, display electronics, contacts 212 and batteries 214 previously described. Alternatively, the contacts 212 may be supported at another position on the inner surface of the outer housing 404 and linked to the microprocessor 202 and batteries 214 by conductive paths or wires. The display mount 112 shown in FIG. 1 may be disposed on top of the insert or may be integral with the insert. The display mount 112 is configured to support the display 210. The display 210 may be larger than the recess 442 and may therefore protrude from the outer housing 404. Alternatively, both the display mount 112 and display 210 may be configured to be received by the recess 442 such that the display 210 is flush with the outer surface of the outer housing 404. The contacts 212 are configured to contact the encoded member 406 in order to facilitate a determination of the rotational position of the encoded member 406, as will be described in more detail with reference to FIGS. 7 to 10.

The dose setting mechanism 400 illustrated in FIG. 3-6 is configured to be re-set to an initial position after the medicament in the attached drug cartridge has been expelled. This allows a new cartridge to be inserted and the drug delivery device 100 to be re-used. This re-setting may be achieved by pushing axially on the distal end of the spindle 414 i.e. the end which usually engages with the drug cartridge and does not require any mechanism associated with removal of a cartridge holder. As illustrated in FIGS. 3 and 4, when the first driver portion 407 is pushed axially towards the second driver portion 412 (i.e., pushed in a proximal direction) the driver 409 is de-coupled from the rest of the dose setting mechanism 400.

An axial force on the spindle 414 causes the spindle 414 to rotate due to its threaded connection to the inner housing 408. This rotation and axial movement of the spindle 414 in turn causes the first driver portion 407 to move axially towards the second driver portion 412. This will eventually de-couple the first driver portion 407 and second driver portion 412.

This axial movement of the first driver portion 407 towards the second driver portion 412 results in certain advantages. For example, one advantage is that the metal spring 401 will compress and will therefore close the Gap 'a' illustrated in FIGS. 3-5. This in turn prevents the clutch 405 from disengaging from the clicker 420 or from the encoded member 406. The second driver portion 412 is prevented from rotation since it is splined to the clutch 405. The clicker 420 is splined to the inner housing 408. Therefore, when the Gap 'a' is reduced or closed up, the second driver portion 412 cannot rotate relative to either the inner housing 408 or the encoded member 406. As a consequence, the encoded member 406 cannot rotate relative to the inner housing 404. If the encoded member 406 is prevented from rotating then, as the spindle 414 is retracted back into the dose setting mechanism 400 and thereby re-set, there will be no risk of the encoded member 406 being pushed out of the proximal side of the dose setting mechanism 400 as a result of a force being applied on the spindle 414.

Another advantage of a dose setting mechanism 400 comprising an inner housing 408 is that the dose setting mechanism 400 can be designed, with a slight modification, as a drug delivery device platform that is now capable of supporting both re-settable and non-resettable drug delivery devices. As just one example, to modify the re-settable dose setting mechanism 400 variant illustrated in FIGS. 3-6 into a non-resettable drug delivery device, the first component part 410 and the second component part 411 of the first driver portion 407 and the second driver portion 412 can be moulded as one unitary part. This reduces the total number of drug delivery device components by two. Otherwise, the drug delivery device illustrated in FIGS. 3-6 could remain unchanged. In such a disposable device, the second housing part 106 would be fixed to the first housing part 104 or alternatively made as a single one piece body and cartridge holder.

The dose setting mechanism described above is merely one example of a mechanism suitable for supporting the encoded member 406 and for implementing the present invention. It will be apparent to the skilled person that other mechanisms may also be suitable. For example, a mechanism which does not include an inner housing 408, but in which the encoded member 406 is still visible to the sensor 112 would be equally suitable.

Figure 7:
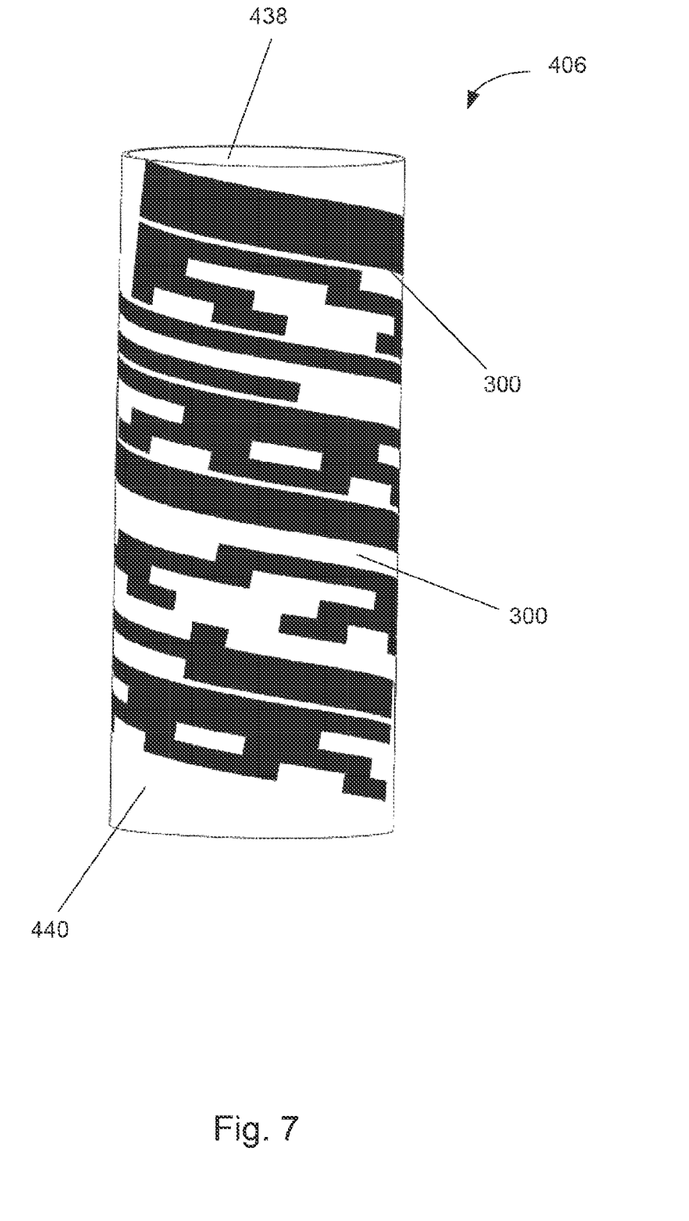
FIG. 7 shows an encoded member according to an embodiment of the invention.

FIG. 7 illustrates the encoded member 406. The encoded member 406 is a hollow cylinder having an outer surface 440 and an inner surface 438. The outer surface 440 comprises a number of helical tracks 300 arranged adjacent to one another. Each track 300 is comprised of conductive and non-conductive segments. In FIG. 7, the conductive segments are shown in black and the non-conductive segments are shown in white. The inner surface 438 of the member 406 may have a helical thread (shown as inner groove 436 in FIGS. 3 to 5). This thread 436 may extend over a single turn or over a partial turn. Alternatively, this thread 436 may comprise several turns. The member 406 may be made of a plastic material. The encoded member 406 is configured to be incorporated into the drug delivery device 100 as shown in FIGS. 3 to 5. The inclusion of an inner housing 408 enables the encoded member 406 to have a helical thread 436 on the inner surface 438 rather then the outer surface 440. This results in a number of advantages. For example, this results in the advantage of providing more surface area along the outer surface 440 of the encoded member 406 for the helical tracks 300. Another advantage is that this inner groove 436 is now protected from dirt ingress. In other words, it is more difficult for dirt to become logged in this inner groove interface than if the groove were provided along the outer surface 440 of the encoded member 406. This feature is particularly important for a re-settable drug delivery device which is required to function over a much longer period of time compared to a non-resettable device.

Figure 8:
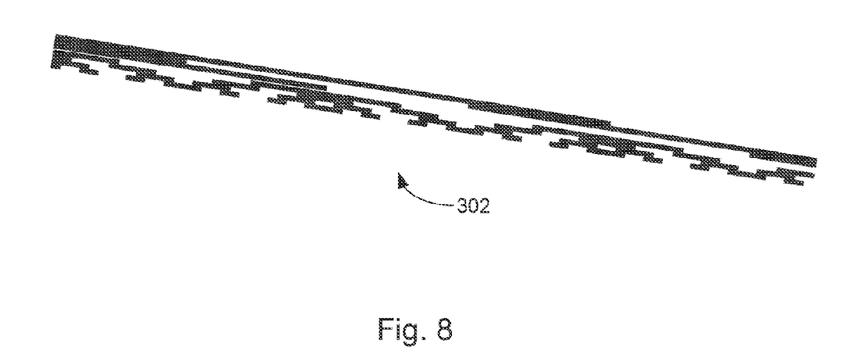
FIG. 8 shows a coded strip suitable for use in manufacturing the encoded member of FIG. 7.

The helical tracks 300 formed on the outer surface 440 of the member 406 may be formed by wrapping one or more metallic strips 302 around the member 406. A single metallic strip 302 suitable for this purpose is shown in FIG. 8. The metallic strip 302 may have a non-conductive backing to support the metallic layer. The non-conductive backing may have an adhesive on the reverse side for securing the strip 302 to the outer surface 440 of the member 406.

The helical tracks 300 may be split into two banks of tracks. The two banks of tracks may be separated by a non-conductive strip. In some embodiments, the outer surface 440 of the member 406 comprises seven helical tracks 300 arranged into a first bank of three tracks and a second bank of four tracks. In some embodiments, a first metallic strip comprises the first bank of helical tracks and a second metallic strip comprises the second bank of tracks.

In some other embodiments, the tracks 300 may be comprised of conductive ink printed onto a non-conductive substrate. This non-conductive substrate may be the member 406 itself or a secondary substrate which is subsequently attached to the member 406.

An electrical conduction path (not shown) may join the two banks of tracks 300. The switch 216 is disposed in this electrical conduction path. The switch 216 is configured to connect electrically the two banks of tracks 300 when the device 100 is idle or when a drug dose is being set by rotation of the rotatable dial 108. The switch 216 is configured to isolate electrically, or disconnect, the two banks of tracks 300 when the selected drug dose is being delivered. The switch 216 is coupled to the dose button 416 supported by the rotatable dial 108, such that when the button is depressed, the switch 216 disconnects the two banks of tracks 200.

Figure 9:
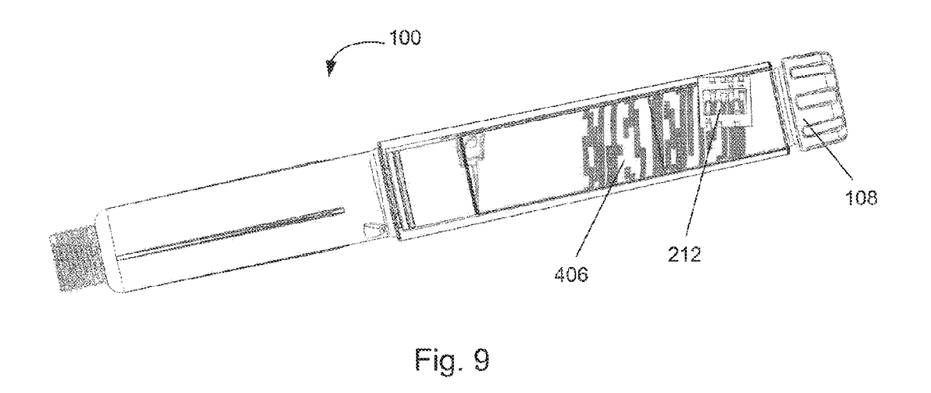
FIG. 9 shows an internal view of a drug delivery device with the encoded member of FIG. 7 mounted in position.

Each of the contacts 212 is configured to engage a respective one of the helical tracks 300 on the encoded member 406. FIG. 9 is an internal view of the drug delivery device 100 showing the relative positions of the encoded member 406 and contacts 212 in an initial configuration. The contacts 212 are shown supported in the recess 442. The contacts 212 may be biased against the outer surface 440 of the coded member 406 in order to provide a stable electrical connection. The contacts 212 are shown divided into a first bank of three contacts and a second bank of four contacts. The contacts 212 are inclined relative to the longitudinal axis of the device 100 by the same degree as the pitch of the helical tracks 300. The pitch of the helical tracks 300 is the same as the pitch of the groove guide 436 of the encoded member 406 which engages with the inner housing groove 432. Therefore, when the encoded member 406 rotates and moves axially within the housing 102, the helical tracks 300 are always positioned directly underneath the contacts 212.

The microprocessor 202 is configured to address each of the contacts 212 individually. The microprocessor 202 is also configured to control the flow of electricity from the batteries 214 to each contact. However, when the batteries 214 provide a signal having a voltage to one of the contacts, certain others of the contacts may also be energized by virtue of being in electrical connection with the first contact via the conductive segments of the helical tracks 300. Thus, the batteries may provide a voltage to a first of the contacts (for example) and the microprocessor 202 may detect signals from each of the contacts which are energized by their electrical connection to the first contact through the tracks 300. Since the microprocessor 202 can address the contacts 212 individually, it is able to apply a signal to different contacts in a sequence, each time monitoring signals from the other contacts 212.

The conductive and non-conductive segments of the helical tracks 300 may be arranged to form a type of Gray code, or reflected binary code. A Gray code is a binary coding system in which only one binary bit changes value between each successive encoded value. An exemplary Gray code is depicted in the table 500 of FIG. 10. FIG. 10 is a tabular representation of the metallic strip 302 shown in FIG. 8. The columns labelled 1 to 7 represent the helical tracks 300 of the encoded member 406. In FIGS. 7 to 10, the darker regions represent a conductive segment and the lighter regions represent a non-conductive segment. A code digit with a value of "1" is represented by a conductive segment and a value of "0" is represented by a non-conductive segment. The Gray code shown in FIG. 10 is arranged such that at position "0" the contacts 212 all have a value of "1". This arrangement aids with error checking of the device 100 as any inoperable contacts will not initially register a value.

Where the drug delivery device 100 shown in FIG. 1 is an insulin pen type injection device, users may need to set an insulin dose of between 1 and 80 International Units. A seven bit encoding system as shown means that $2^7=128$ positions can be encoded on the encoded member 406. Thus the full 0-80 unit dial-able dose for an injection device can be absolutely encoded with redundant positions available. The last column of table 500 shows the binary result obtained by the microprocessor 202 when signals from the contacts 212 in each rotational position are received. The first column of table 500 shows the dose unit which the binary result encodes.

Each conductive segment within each bank is electrically connected to every other conductive segment within that bank. The Gray code of the depicted embodiment is designed such that for all increments between 0-80 units there is at least one segment within each bank of tracks 300 which is a conductive segment. Thus, in all rotational positions of the encoded member 406, when a voltage is provided to the contacts 212, at least one contact in each bank will register a binary value of "1". This allows the use of a commutation encoder method as described without the need for a dedicated power or ground line. Furthermore, as the switch 216 is incorporated into a conductive path joining the two banks, no dedicated switch signal track is required.

When a user of the device 100 rotates the rotatable dial 108 to set a drug dose, the microprocessor 202 may be activated and may be controlled by software stored in the ROM 204 to execute a cyclic check on the contacts 212 to determine the absolute rotational position of the encoded member 406, and hence the drug dose which has been dialled. The microprocessor 202 may also determine the status of the switch 216 and hence whether the device 100 is in dialling mode or dispensing mode. The microprocessor 202 may also be configured to determine the number of drug units which have been delivered.

Figure 11:
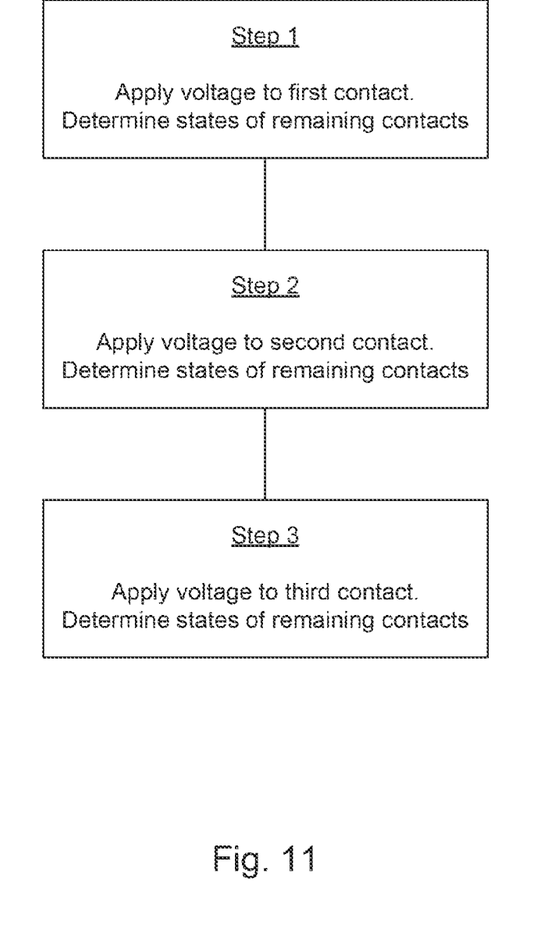
FIG. 11 is a flow chart illustrating the steps involved in determining the rotational position of the encoded member.

Referring to FIG. 11, the process of determining a dialled dose is now described. In order to determine the drug dose which has been dialled, the microprocessor 202 first causes a voltage to be applied to the first contact and then determines which of the remaining six contacts are energised (Step 1). The microprocessor 202 then causes a voltage to be applied to the second contact and determines which of the remaining six contacts are energised (Step 2). Finally, this process is repeated for the third contact (Step 3). If no contacts in the second bank (i.e. contacts four to seven) are energised in any of these three steps, then the microprocessor 202 determines that the device 100 is in dispensing mode i.e. that a dose is currently being delivered.

When the device 100 is in a dose dialling mode, the combination of readings taken in these three steps is sufficient to determine the full seven bit code and hence the drug dose which has been dialled. The microprocessor 202 may achieve this by searching a lookup table stored in the ROM 204, the lookup table providing a conversion from a seven bit binary code result to a dose unit dialled.

For example, in position "0" each of the seven helical tracks 300 has a conductive segment. Therefore, if the device is not in dispensing mode, the microprocessor 202 reads a positive result at contacts 2 to 7 in step 1, a positive result at contacts 1 and 3 to 7 at step 2 and a positive result at contacts 1, 2 and 4 to 7 in step 3. In effect the binary result "1111111" is read at each step and the device 100 is determined to be in position "0" and in dose dialling mode.

If the device is in dispensing mode, i.e. if the dose button 416 is depressed, then the switch 216 causes the first and second banks of tracks 300 to be electrically disconnected. In this situation, the microprocessor 202 reads a positive result only at contacts 2 and 3 in step 1, contacts 1 and 3 at step 2 and contacts 1 and 2 in step 3. The microprocessor 202 therefore determines a binary reading of "1110000". Since each bank of tracks 300 is known to contain at least one conductive segment at each rotational position, the microprocessor 202 determines that the switch 216 is in the disconnect position and that the device is in dispensing mode. The microprocessor 202 may be configured to control the display 210 to show specific symbol(s) or text to indicate to a user of the device 100 that the device is in dispensing mode. Alternatively, the display 210 may be disabled when the device 100 is in dispensing mode.

As a further example, in position "15" the second helical track comprises a non-conductive segment. Therefore, if the device 100 is in a dose dialling mode, in the first step of FIG. 11, the binary code determined by the microprocessor 202 is "1010011". In the second step of FIG. 11, the binary code is "0000000" (because there is no conductive track at the location of the second contact) and in the third step of FIG. 11, the binary code is "1010011". The microprocessor 202 is therefore able to determine the position to be "15".

When dispensing a selected dose, if for any reason the user does not dispense the full dose, the display 210 may be configured to show the dose which is remaining to be dispensed. In this situation, the microprocessor 202 may determine the drug dose which has been dispensed by subtracting a remaining drug dose from the initially dialled drug dose.

Although a seven bit system has been described, the method is equally applicable for any number of contacts greater than three. The seven bit system is preferred as it allows the full 0-80 unit dose range to be absolutely encoded.

In some alternative embodiments of the invention, the encoded member 406 may comprise a metallic ring having protrusions round the circumference representing the conductive "1" value of the binary code. The recesses representing binary "0" can then be filled with a non-conductive material. No dedicated power or ground line is required in this embodiment.

In an alternative embodiment of the invention the operation of the switch 216 is reversed. In this alternative embodiment, the switch 216 is configured to disconnect electrically the two banks of tracks 300 when the device 100 is idle or when a drug dose is being set by rotation of the rotatable dial 108. The switch 216 is configured to connect the two banks of tracks 300 when the selected drug dose is being delivered. The switch 216 is coupled to the dose button 416 supported by the rotatable dial 108, such that when the button is depressed, the switch 216 connects the two banks of tracks 300.

The microprocessor 202 may perform the cyclic check described above while the encoded member is rotating, i.e. while the device is being dispensed. Therefore the same method as described above may be used to determine a dispensed dose, rather than a dialled dose.

Having determined the drug dose which has been dispensed, the microprocessor 202 may store the result in the ROM 204. The display 210 may be controlled to display the result of the dispensed dose determination. The display 210 may display the result of the dispensed dose determination for a predetermined time, for example 60 seconds. Alternatively or in addition, the dispensed dose history may be retrieved electronically from the ROM 204 by a user of the device 100 or by a health care professional. During dialling of the device, the dialled dose may be indicated to the user in any conventional way, for example by use of numerals printed on the number sleeve. Alternatively or in addition, a more complex cyclic check may be performed on the contacts 212 in order to determine the absolute rotational position of the encoded member 406 during dialling. This may involve checking each of the seven contacts in turn. In some other embodiments, the dialled dose is not determined or indicated to the user.

It will be appreciated that the above described embodiments are purely illustrative and are not limiting on the scope of the invention. Other variations and modifications will be apparent to persons skilled in the art upon reading the present application. Moreover, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N- palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38 Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A drug delivery device comprising;
   a housing;
   a plurality of contacts; and
   a cylindrical member configured to be rotatably supported inside the housing, wherein the outer surface of the cylindrical member is provided with a plurality of tracks together forming an encoder, each track comprising conductive segments and non-conductive segments, and wherein the cylindrical member is supported in the housing such that each track is engaged by a respective one of the plurality of contacts,
   wherein the plurality of tracks are arranged into first and second banks of tracks; and a switch configured:
      in a first position, to electrically connect the first and second banks of tracks; and
      in a second position, to electrically isolate the first and second banks of tracks.

2. A drug delivery device as claimed in claim 1, wherein the plurality of tracks are helical tracks and wherein the housing and the cylindrical member are configured such that the cylindrical member moves in a first axial direction relative to the housing when rotated in a first rotational direction relative to the housing.

3. A drug delivery device as claimed in claim 1, wherein the conductive and non-conductive segments of the plurality of tracks are arranged as a Gray code.

4. A drug delivery device as claimed in claim 1, wherein the conductive segments within each of the first and second banks are electrically connected to all of the conductive segments in the bank.

5. A drug delivery device as claimed in claim 1, further comprising a user actuated plunger configured to cause expulsion of a drug from the drug delivery device and wherein depression of the plunger causes the switch to switch from the first position to the second position.

6. A drug delivery device as claimed in claim 1, wherein the outer surface of the cylindrical member is provided with seven helical tracks.

7. A drug delivery device as claimed in claim 1, wherein each contact is configured to engage a first segment of each respective track when the cylindrical member is in a first rotational position, and wherein each first segment is a conductive segment.

8. A drug delivery device as claimed in claim 1, wherein the device further comprises;
   a display; and
   a processor configured to receive and interpret electrical signals from the contacts and to control the operation of the display.

9. A drug delivery device as claimed in claim 8, wherein the processor is configured to control application of electrical signals to the contacts.

10. A drug delivery device as claimed in claim 9, wherein the processor is configured to cause an electrical signal to be applied to a first one of the contacts and simultaneously to monitor signals at the others of the contacts, and subsequently to cause an electrical signal to be applied to a second one of the contacts and simultaneously to monitor electrical signals at the others of the contacts.

11. A drug delivery device as claimed in claim 10, wherein the processor is configured to apply an electrical signal to each of the contacts relating to the first bank in a sequence and to process the resulting electrical signals at the other contacts to determine whether the switch is closed.

12. A drug delivery device as claimed in claim 10, wherein the processor is configured to cause an electrical signal to be applied to at least the first one of the contacts and simultaneously to monitor signals at the others of the contacts in order to determine a position of the cylindrical member.

13. A drug delivery device as claimed in claim 12, wherein the processor is further configured to determine a selected drug dose by searching a lookup table providing a conversion from a position of the cylindrical member to a selected drug dose.

14. A drug delivery device as claimed in claim 13, wherein the processor is further configured to determine a delivered drug dose by subtracting a remaining drug dose from the selected drug dose.

* * * * *